US012618034B2

(12) United States Patent
Krüger et al.

(10) Patent No.: US 12,618,034 B2
(45) Date of Patent: May 5, 2026

(54) DEVICE AND METHOD FOR CELL CULTIVATION

(71) Applicant: LPKF LASER & ELECTRONICS AG, Garbsen (DE)

(72) Inventors: Robin A. Krüger, Hannover (DE);
Antonia Heine-Dank, Garbsen (DE);
Oktavia Ostermann, Hannover (DE);
Bernd Rösener, Porta Westfalica (DE);
Malte Schultz-Ruhtenberg, Wunstorf (DE)

(73) Assignee: LPKF LASER & ELECTRONICS AG, Garbsen (DE)

( * ) Notice: Subject to any disclaimer, the term of this patent is extended or adjusted under 35 U.S.C. 154(b) by 657 days.

(21) Appl. No.: 18/004,567

(22) PCT Filed: May 6, 2022

(86) PCT No.: PCT/EP2022/062301
§ 371 (c)(1),
(2) Date: Jan. 6, 2023

(87) PCT Pub. No.: WO2022/234096
PCT Pub. Date: Nov. 10, 2022

(65) Prior Publication Data
US 2023/0250376 A1      Aug. 10, 2023

(30) Foreign Application Priority Data
May 7, 2021    (DE) .......................... 102021204675.4

(51) Int. Cl.
*C12M 1/32* (2006.01)
*C12M 1/00* (2006.01)
*C12M 1/12* (2006.01)

(52) U.S. Cl.
CPC ............ *C12M 23/12* (2013.01); *C12M 23/20* (2013.01); *C12M 25/06* (2013.01)

(58) Field of Classification Search
CPC ...... C12M 23/12; C12M 23/20; C12M 23/40; C12M 25/06
See application file for complete search history.

(56) References Cited

U.S. PATENT DOCUMENTS

| | | | |
|---|---|---|---|
| 9,964,556 B2 | 5/2018 | Wenezel et al. | |
| 2009/0013724 A1 | 1/2009 | Koyo et al. | |

(Continued)

FOREIGN PATENT DOCUMENTS

| | | | | |
|---|---|---|---|---|
| CN | 107338183 | * | 11/2017 | ........... C12M 29/04 |
| CN | 107338183 A | | 11/2017 | |

(Continued)

OTHER PUBLICATIONS

International Search Report from the corresponding International Patent Application No. PCT/EP2022/062301, dated Sep. 17, 2022.

(Continued)

*Primary Examiner* — Michael L Hobbs

(74) *Attorney, Agent, or Firm* — Greer, Burns & Crain, Ltd.; Steven P. Fallon

(57) ABSTRACT

A carrier suitable for the cultivation of cells includes a plate-shaped carrier, e.g. made of glass, silicon or plastic or a combination thereof. At least one first recess is formed in the carrier and extends over a first thickness section of the carrier. An arrangement of second recesses extends from the first recess into a second thickness section of the carrier adjacent to the first thickness section. The first thickness section can have a thickness of a few micrometers to a few centimeters. The second recesses extending from a first recess into the second thickness section, each forming a (Continued)

second arrangement, form wells suitable for receiving cells and/or synthetic particles, e.g. made of plastic or glass.

19 Claims, 6 Drawing Sheets

(56)                    References Cited

U.S. PATENT DOCUMENTS

| | | | |
|---|---|---|---|
| 2010/0068793 A1 * | 3/2010 | Ungrin ................. | C12N 5/0603 |
| | | | 435/283.1 |
| 2012/0258459 A1 * | 10/2012 | Huang .................. | B01L 3/5021 |
| | | | 210/767 |
| 2017/0256422 A1 | 9/2017 | Ambrosius et al. | |
| 2022/0089478 A1 | 3/2022 | Krüger et al. | |

FOREIGN PATENT DOCUMENTS

| | | | | |
|---|---|---|---|---|
| DE | 102019217466 A1 | 5/2021 | | |
| DE | 102020209825 A1 | 2/2022 | | |
| EP | 1867612 A1 | 12/2007 | | |
| EP | 2011857 A1 | 1/2009 | | |
| WO | WO-2015195941 A1 * | 12/2015 | ............ | C12M 23/12 |
| WO | 2016/076795 A1 | 5/2016 | | |

OTHER PUBLICATIONS

International Preliminary Report on Patentability from the corresponding International Patent Application No. PCT/EP2022/062301, dated Oct. 24, 2023.

* cited by examiner

Fig. 5
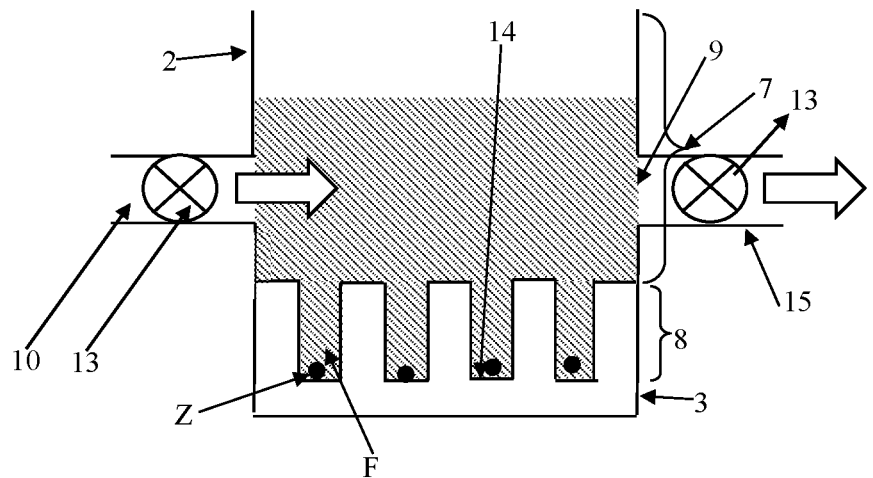
Fig. 6
Fig. 7
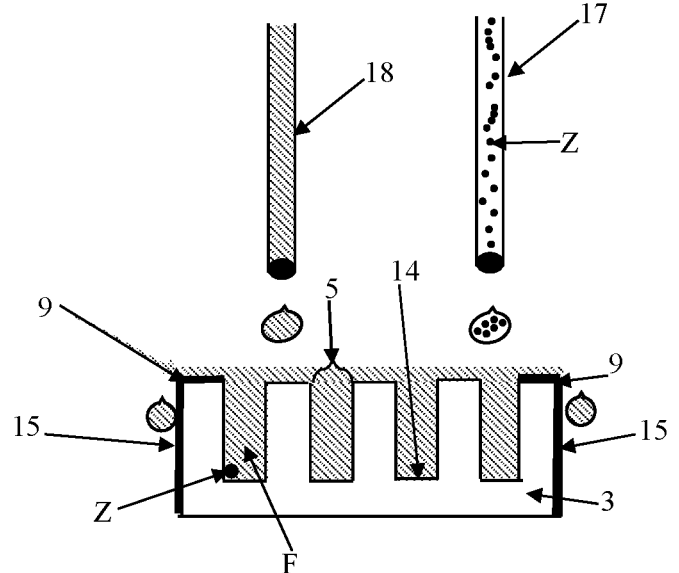

Fig. 8
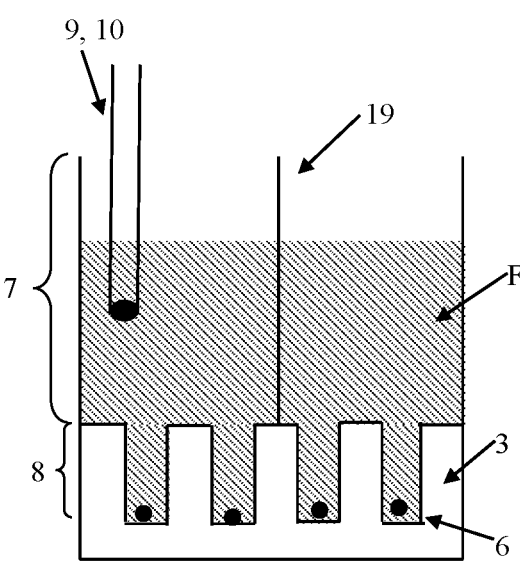
Fig. 9A
Fig. 9B
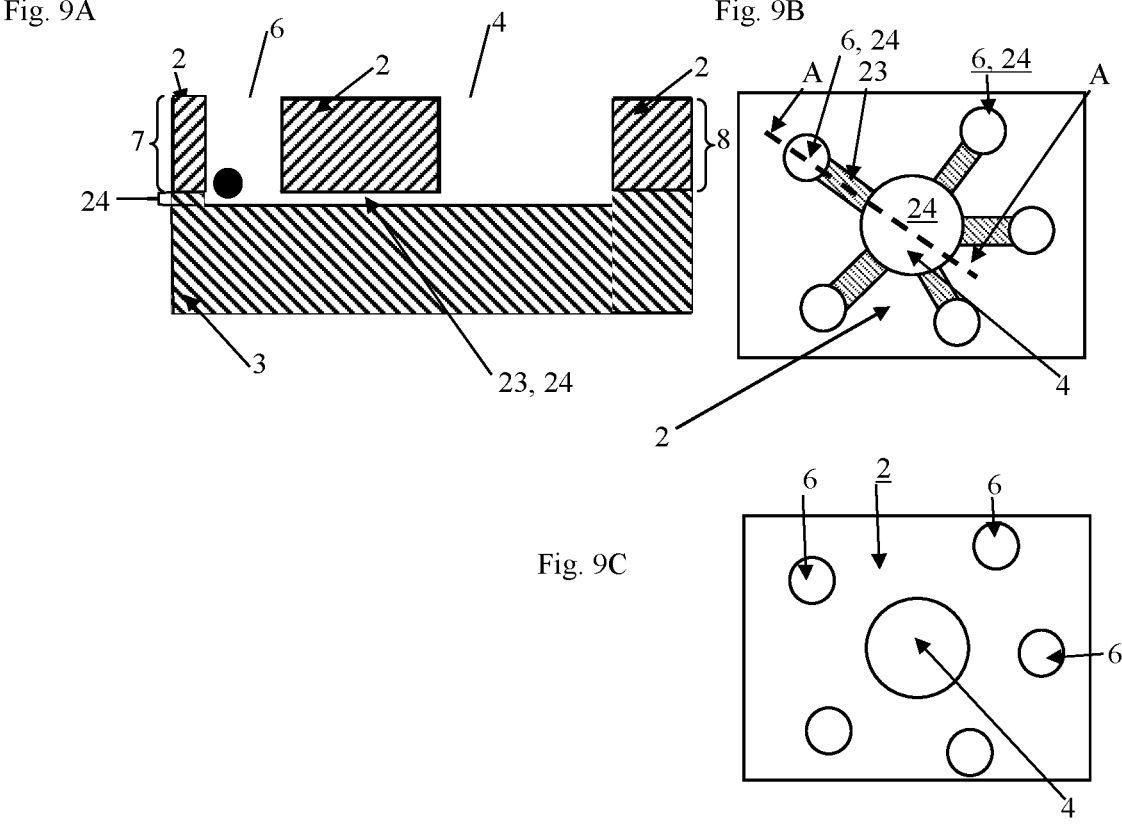
Fig. 9C

DEVICE AND METHOD FOR CELL CULTIVATION

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2022/062301, which was filed May 6, 2022, which application claimed priority from German application 10 2021 204 675.4, which was filed May 7, 2021.

FIELD OF THE INVENTION

A filed of the invention concerns cell cultivation devices, use of such devices and methods of cell cultivation.

BACKGROUND

Conventionally, for such methods, so-called microtiter plates are used as devices for cell cultivation and for conducting biological experiments. Microtiter plates have wells with a volume of e.g. approx. 300 μl. One biological experiment can be performed per well, and a large amount of reagents is therefore required per well. In addition, microtiter plates are comparatively large and only provide space for typically 96 and up to 1536 parallel experiments. Locating individual cells in these wells, e.g. using a light microscope, is laborious.

This poses major challenges for high-throughput experiments in which specific cell types are to be cultured and studied, e.g. cell line development, monoclonal antibody development, synthetic biology, cell therapy, immuno-therapy, stem cell research.

The use of highly miniaturized wells, e.g. volumes reduced by a factor of 100,000, is technically possible, but brings new challenges, in particular evaporation, feeding of nutrients, concentration of metabolic products and cell migration. The latter arises from the movement of the cells under their own power or from turbulence when refilling reagents or media, when moving carriers, from heating and convection.

For most biomedical developments, constant conditions must be ensured in each individual experiment. For the approval of medical products, monoclonality must be demonstrated. DE 10 2020 209 825 A1 describes a method for manufacturing a plastic part having a glass insert from a prefabricated plastic part having a circumferential weld web and a glass insert, which has through-holes spaced apart in a circumferentially closed abutment region, and heating the weld web and pressing the glass insert with its abutment region against the weld web of the plastic part to produce a joint region in which plastic rests in the abutment region and has passed through the through-holes of the glass insert.

DE 10 2019 217 466 A1 describes glass reaction vessels formed as recesses of at least 30 μm depth in a one-piece glass plate or in two interconnected glass plates. The recesses can have a section extending into the glass plate only up to a first thickness section, from which further smaller recesses can extend up to a deeper second thickness section.

WO 2016/041544 A1 generally describes a method preferred for making recesses in glass.

SUMMARY OF THE INVENTION

The invention provides an alternative method for the cultivation of cells and a carrier suitable for use in the method, the carrier having recesses for cells, in order to hold cells in their separate wells and yet to contact several wells with a common volume of medium forming a common supply of medium. Preferably, the carrier is adapted to selectively drain or withdraw liquid, in particular cell culture medium, from recesses.

An embodiment of the invention provides a carrier for cultivating cells. The carrier includes at least one first recess) extending over a first thickness section from a first surface of the carrier up to a second thickness section which is adjacent to the first thickness section and in which an arrangement of second recesses extends from the first recess. The second recesses have an aspect ratio of depth to diameter of at least 1:1 and a diameter of at most 1 mm. The carrier has an outlet whose cross-section opens in or adjacent to the first thickness section.

BRIEF DESCRIPTION OF THE DRAWINGS

The invention is now described in more detail by means of examples with reference to the figures, which show schematically in FIG. 1 an embodiment of the invention, FIG. 2 an embodiment of the invention with supply conduit from the second surface of the carrier, FIG. 3 an embodiment of the invention with supply conduit and outlet from the second surface of the carrier, FIG. 4 embodiments of the invention in top view, FIG. 5 an embodiment of the invention with supply conduit and outlet, FIG. 6 a further embodiment of the invention with supply conduit and outlet, FIG. 7 a further embodiment of the invention, FIG. 8 a further embodiment of the invention, FIGS. 9A in cross-section and 9B in plan view on a carrier an embodiment, FIG. 9C a first partial carrier in plan view, FIG. 10 a further embodiment of the invention, FIGS. 11A and 11B a further embodiment of the invention and FIG. 12 a further embodiment.

DETAILED DESCRIPTION OF THE PREFERRED EMBODIMENTS

Figure 1:
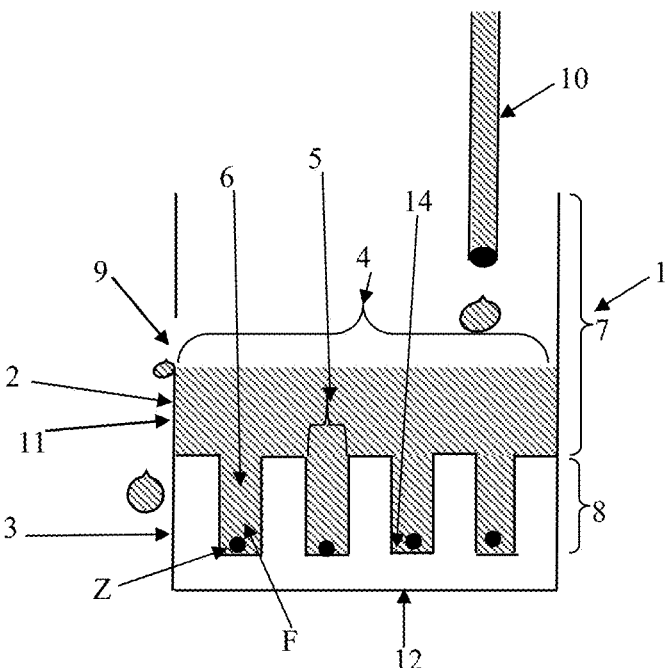

The present invention relates to a device, the use of the device for cell cultivation, and a method of cell cultivation using the device. The device is characterized by having separate wells for receiving cells, the wells being in contact with a larger volume so that an exchange of liquid can occur. The wells have a large aspect ratio of depth to diameter that retains cells in the wells or suppresses discharge of cells from the wells into the larger volume that is in contact with the wells. The method has the advantage of holding cells, which can be single cells or multiple cells, in their wells, wherein multiple wells are in contact with a common volume of medium. By holding cells in wells having a large aspect ratio, the method has the advantage that cells are identifiable by the wells containing them and are observable over a longer cultivation period, e.g., over 1 to 10 d. Due to the large aspect ratio of the wells in combination with a variation of the diffusion rate, e.g. by varying the inflow and outflow of medium, either metabolic products can accumulate separately for each well and be assigned to the well and cells contained therein, or particularly constant conditions are created by rapid exchange of medium and removal of metabolic products.

The cultivation of cells in the present case is an in vitro method, in particular the cultivation of cells in medium which keeps the cells alive and/or is suitable for cell propagation. The cells are, for example, animal cells, in particular human cells, plant or fungal or yeast cells or bacteria. The cultivation can e.g. be carried out for the analysis and/or isolation of cells, optionally with addition of an active agent to the medium.

The invention provides a carrier which is suitable for the cultivation of cells and which preferably is a plate-shaped carrier, e.g. made of glass, silicon, or plastic, or a combination thereof, in which at least one first recess is formed which extends over a first thickness section of the carrier, wherein an arrangement of second recesses extends from the first recess into a second thickness section of the carrier adjacent to the first thickness section. The first thickness section can have a thickness of a few micrometers to a few centimeters. The second recesses, which extend from a first recess into the second thickness section and each form a second arrangement, form wells suitable for receiving cells and/or synthetic particles, for example made of plastic or glass. The second recesses, also referred to as wells, have a large aspect ratio of depth to diameter determined in the plane of the first thickness section adjacent the second thickness section or at half the height of the second thickness section. For example, the wells have an aspect ratio of depth to diameter of at least 1:1, preferably at least 2:1, preferably at least 5:1, preferably at least 10:1, preferably at least 20:1, preferably at least 40:1, preferably at least 50:1, wherein the wells have a diameter of at most 1000 μm, preferably at most 900 μm, preferably at most 800 μm, preferably at most 700 μm, preferably at most 600 μm, preferably at most 500 μm, preferably at most 400 μm, preferably at most 300 μm, preferably at most 200 μm, preferably at most 100 μm, preferably at most 90 μm, preferably at most 80 μm, preferably at most 70 μm, preferably at most 60 μm, preferably at most 50 μm, preferably at most 40 μm, preferably at most 30 μm, preferably at most 20 μm, preferably at most 10 μm, preferably at most 5 μm.

The diameter of the wells can be adapted to the size of the cells, for example to be able to arrange cells in a stack or to bring them into contact with one another. The cross-section of the individual wells can be rectangular, A-shaped, V-shaped or waisted. The bottom of the wells can be flat, pointed (conical), or rounded. The bottom can have further microstructures.

The first thickness section is limited in a plane by the first surface of the carrier in which the cross-sectional openings of the first recesses lie, and in a plane spaced therefrom by the cross-sectional openings of the second recesses. The cross-sectional openings of the second recesses are spaced apart by surface regions of the carrier, which is in particular a second partial carrier. Further preferably, these surface regions and the cross-sectional openings of the second recesses lie in a common plane. Preferably, the cross-sectional openings of the second recesses are directly adjacent to the cross-section of a first recess. Alternatively, the second recesses can be spaced from a first recess and can be connected thereto by means of a transition conduit. In a preferred embodiment, such a transition conduit is formed as a region-wise spacing between a first and a second partial carrier, wherein first and second recesses are formed in the first partial carrier and the bottom thereof is formed by the second partial carrier, respectively. The second partial carrier has a recess which forms the region-wise spacing between the first and second partial carriers for the cross-section of the transition conduit.

The arrangement of the second recesses can be arbitrary, but is preferably arranged regularly, e.g., in parallel rows, in nodes of a lattice, and/or at equal intervals in each case, which is, e.g., a square or hexagonal lattice. An arrangement of the second recesses extending adjacent to a first arrangement can e.g. have at least 1, preferably at least 10, preferably at least 20, preferably at least 30, preferably at least 40, preferably at least 50, preferably at least 60, preferably at least 70, preferably at least 80, preferably at least 90, preferably at least 100, preferably at least 200, preferably at least 300, preferably at least 400, preferably at least 500, preferably at least 600, preferably at least 700, preferably at least 800, preferably at least 900, preferably at least 1000, preferably at least 2000, preferably at least 3000, preferably at least 4000, preferably at least 5000, preferably at least 6000, preferably at least 7000, preferably at least 8000, preferably at least 9000, preferably at least 10.000, preferably at least 50,000, preferably at least 100,000, preferably at least 500,000, preferably at least 1,000,000, preferably at least 10,000,000, preferably at least 50,000.000, preferably at least 100,000.000 second recesses which are arranged at a distance of at most 10 mm, preferably at most 9 mm, preferably at most 8 mm, preferably at most 7 mm, preferably at most 6 mm, preferably at most 5 mm, preferably at most 4 mm, preferably at most 3 mm, preferably at most 2 mm, preferably at most 1 mm, preferably at most 900 μm, preferably at most 800 μm, preferably at most 700 μm, preferably at most 600 μm, preferably at most 500 μm, preferably at most 400 μm, preferably at most 300 μm, preferably at most 200 μm, preferably at most 100 μm, preferably at most 90 μm, preferably at most 80 μm, preferably at most 70 μm, preferably at most 60 μm, preferably at most 50 μm, preferably at most 40 μm, preferably at most 30 μm, preferably at most 20 μm, preferably at most 10 μm, preferably at most 9 μm, preferably at most 8 μm, preferably at most 7 μm, preferably at most 6 μm, preferably at most 5 μm, preferably at most 4 μm, preferably at most 3 μm, preferably at most 2 μm, preferably at most 1 μm from one another.

The cross-sectional opening of the first recess is in the plane of a first surface of the carrier, such that the first recess opens in the plane of the first surface of the carrier. The carrier is characterized by an outlet, the cross-section of which opens in or adjacent to the first thickness section, wherein the cross-sectional opening of the outlet preferably is adjacent to the plane of the first surface of the carrier or which is open to the plane of the first surface of the carrier, the outlet being connected to the first recess. The outlet is formed in the carrier, for example in the form of a trench which is open to the plane of the first surface of the carrier. Alternatively, the outlet can be a conduit extending into the first recess. Generally, the outlet is arranged to discharge liquid, in particular medium, from the first recess. Therein, the outlet can be arranged to discharge liquid solely by the action of gravity and/or by means of a pump and/or by applying positive pressure to the first recess. The outlet can have a cross-section that extends into the carrier to a depth that is a portion of, for example, 1% to 95% of the first thickness section. Such an outlet is for draining or removing liquid extending in the first recess up into the cross-section of the outlet, particularly at a level of liquid in the first recess up to the plane of the first surface of the carrier. The outlet can extend circumferentially around at least one, preferably exactly one, first recess such that the outlet forms a circumferential recess in the carrier around a first recess, the circumferential recess being limited by the carrier which, at a distance from this outlet, extends into the plane of its first surface. In the embodiment of the outlet as a recess or hydrophilic surface formed circumferentially around a first recess, exactly one or at least two connection conduits can be connected to this outlet. Optionally, the outlet can additionally form an inlet connected to the first recess, in particular for liquid, e.g. medium, or gas.

The rate at which liquid exits or is withdrawn at the outlet can be controlled by the thickness of the first thickness section, by the rate at which liquid is supplied, or by inclination of the carrier. The outlet can be carried out as multiple openings, such as holes of various diameters. Outflowing liquid can be collected and analyzed or reused.

In a further embodiment, the carrier can have as an outlet a hydrophilic surface that each comprises exactly one or at least two first recesses, said outlet being enclosed by a hydrophobic surface or coating of the first surface of the carrier. In this embodiment, the hydrophilic surface comprising a first recess as the outlet can lie in the same plane as the first surface of the carrier, which is preferably contiguously hydrophobic. Also in this embodiment, a connection conduit can be arranged in the outlet consisting of a hydrophilic surface section comprising on the carrier, optionally without a recess in the carrier. In the method, the hydrophilic surface of this outlet, even if it lies in the plane of the first surface of the carrier, allows the passage of liquid from the first recess into the connection conduit, with the spreading of the liquid onto the first surface being limited by the hydrophobicity of the first surface adjacent to this outlet.

By means of the outlet and preferably by a connection conduit connected to the outlet, the carrier is set up for a method of cell cultivation in which liquid, in particular cell culture medium, can be selectively drained or removed from recesses. A connection conduit connects the outlet to a tapping point spaced therefrom, which can e.g. be a container for liquid or an analysis equipment. Generally, a connection conduit can be formed in the carrier as a recess having a cross-section open to the surface of the carrier, such as e.g. a trench, or the recess having a circumferentially closed cross-section, such as e.g. a bore passing through the carrier.

In an embodiment, a connection conduit is formed within the carrier and/or on an end surface of the carrier, which connection conduit extends from the first surface of the carrier over the entire cross-section thereof to the second surface thereof. The connection conduit is connected to the outlet opposite the second surface of the carrier so that liquid can flow from the outlet through the connection conduit into the plane of the second surface of the carrier, particularly when the carrier is arranged horizontally with its first surface above the second surface.

In embodiments, the connection conduit directs liquid, whose level in the first recess reaches the cross-section of the outlet and flows through the outlet, to the opposite second surface of the carrier. Therefore, when liquid is supplied into the first recess, liquid whose level reaches the cross-section of the outlet is diverted in a controlled manner and the level will not exceed the cross-section of the outlet and, in particular, the first surface of the carrier. The mouth of the connection conduit in the second surface of the carrier allows liquid emerging there to be removed, e.g. for subsequent analysis, without an additional removal device, e.g. a pipette, coming into contact with the liquid in the first recess.

The surfaces of the connection conduit and the outlet are preferably hydrophilic, further preferably the first surface of the carrier and/or the opposite second surface of the carrier is hydrophobic, e.g., provided with a hydrophobic coating. Optionally, a groove enclosing the mouth is formed in the second surface of the carrier at a distance around the mouth of the connection conduit. A groove in the second surface of the carrier enclosing the mouth of the connection conduit reduces the spreading of liquid emerging from the mouth over the second surface of the carrier.

Preferably, a carrier has at least two first recesses, the first thickness section of which is adjoined in each case by an arrangement of second recesses, wherein each first arrangement is connected by means of at least one outlet to at least one or exactly one connection conduit. In this embodiment, at least two first recesses are connected independently of one another to a connection conduit in each case, so that liquid emerging from the first recess emerges separately for each first recess on the second surface from a connection conduit and can be removed and/or analyzed separately.

Optionally, a carrier has at least two first recesses, the first thickness section of each of which is adjoined by an arrangement of second recesses, wherein the outlet connected to the one first recess opens into another first recess such that the outlet is configured to direct liquid emerging from the one first recess into the other first recess.

Generally, optionally adjacent to the first surface of the carrier, at least one supply conduit can be formed in the carrier, which supply conduit opens into at least one first recess. A supply conduit can be formed, for example, as a trench in the carrier, the cross-section of the trench being open in the plane of the first surface of the carrier. Therein, a reservoir recess extending into the carrier can be connected to the supply conduit at a distance from a first recess. A reservoir recess, e.g., having a depth equal to or less than the depth of the supply conduit, can serve to receive liquid, e.g., cell culture medium, which is metered into the reservoir recess as a reservoir.

The first recesses and the second recesses can be formed in a one-piece carrier, preferably a glass carrier. Recesses in a one-piece carrier can be formed by removing material from an original one-piece carrier, e.g. by laser irradiation followed by etching. Alternatively, the first recesses can be through-holes in a first partial carrier to which a second partial carrier is attached in which the second recesses are formed. When the carrier is formed from at least two partial carriers, the carrier is in two pieces, wherein the partial carriers can be directly connected to one another, for example by bonding, or can be connected to one another by a bonding compound, for example fused glass frit or adhesive. The second recesses can be through holes in the second partial carrier, the cross-sectional opening of which opposite to the first partial carrier is covered by a third partial carrier, or can be blind holes in the second partial carrier. Optionally, the second partial carrier is made of colored glass, the optional third partial carrier is made of transparent glass, and the first partial carrier is made of uncolored or transparent glass. Therein, transparent glass is transparent to light that is irradiated onto the carrier for optical detection and is transparent to light that can emanate from second recesses for optical detection. Colored glass is preferably non-transparent to light that is irradiated onto the carrier for optical detection or is non-transparent to light that can emanate from second recesses for optical detection. Preferably, the carrier, or all partial carriers, are made of glass.

The large aspect ratio of the second recesses causes cells introduced therein to remain in a second recess and allows for a method of cell cultivation in which liquid is introduced into or emerges from the first recess while the cells remain in the second recesses. Therein, the inner volumes of the second recesses are in contact with the inner volume of the first recess, so that an exchange takes place between them, e.g. by diffusion of metabolic products from second recesses into the first recess and of nutrients, dissolved oxygen and possibly added active substances from the first recess into second recesses.

Optionally, a sensor is arranged in a first recess, in one of the second recesses, in the outlet and/or in the inlet, e.g. in a connection conduit. A sensor can be a gas sensor, e.g. for oxygen or carbon dioxide, a pH sensor, temperature sensor, or a binding molecule specific for an analyte, preferably immobilized, e.g. an antibody specific for an analyte in the medium. Further optionally, a same sensor can each be arranged in the inlet and in the outlet, which are connected to an evaluation unit that is set up to detect changes in the sensor signals.

The introduction of liquid into first recesses can be carried out by dropping drops or filling through a conduit which is in contact with the liquid in the first recess, respectively through the cross-sectional opening of the first recess in the plane of the first surface of the carrier. Alternatively, the carrier can have a supply conduit extending from its second surface directly into the first recess, such that the supply conduit is adapted to conduct liquid and/or gas from the second surface into the first recess. Generally, when the carrier is arranged horizontally, its second surface is arranged horizontally and below its first surface, wherein preferably the first and second surfaces are parallel to one another. Alternatively or additionally, a supply conduit can extend through a wall section within the first thickness section in which a first recess is formed so that liquid, e.g., medium for cell culture, can be introduced into the first recess through the supply conduit in the first thickness section.

In the carrier, an outlet can be formed as a conduit in the first thickness section, e.g., in a first recess in a wall opposite a supply conduit.

In an embodiment, the wall extending over the first thickness section and having or enclosing the first recesses can be formed by a first partial carrier adjoining a second partial carrier in which second recesses are formed. Therein, the first partial carrier can be mounted on the second partial carrier, for example by the first partial carrier and the second partial carrier overlapping in the edge region in a displaceable and liquid-tight manner. Optionally, the first partial carrier can be displaceable in perpendicular to the second partial carrier in a liquid-tight manner, so that the first thickness section is adjustable by the displaceability of the first partial carrier relative to the second partial carrier. When first recesses are formed in a first partial carrier, which is liquid-tight and is arranged to be mountable or displaceable relative to the second partial carrier, in which second recesses are formed, the carrier is set up to adjust the level of the liquid in the first recess depending on the position of the first partial carrier relative to the second partial carrier. This is because the outlet, especially if it does not have a valve, discharges liquid from the first recess whose level reaches its cross-section. Therein, the first partial carrier can consist of plastic and the second partial carrier can consist of glass, or the first and second partial carriers can consist of glass, optionally with a slidable seal in the overlap region of the partial carriers. Alternatively, for adjusting the liquid level in the first recess, a valve can be arranged in the inlet and/or in the outlet, by which, for example, in the method the liquid level in the first recess can be adjusted.

In an embodiment, inlets and/or outlets can include one or more valves that regulate one or more connection conduits.

With multiple valves and multiple connection conduits, it is possible to meter different liquids into the first recess in a controlled manner.

In an embodiment, the carrier can consists of a second partial carrier having second recesses arranged therein and a first partial carrier attached thereto having exactly one first recess extending across all second recesses. Generally, and particularly in this embodiment, the first partial carrier can consist of plastic or glass and the second partial carrier can consist of glass with second recesses therein. In embodiments in which the first partial carrier consists of plastic and the second partial carrier consists of glass, it is preferred that the second partial carrier has through-holes in the region of the connection with the first partial carrier and plastic of the first partial carrier extends integrally through these through-holes, for example by plastic of the first partial carrier being pressed into and possibly through these through-holes after heating of first and/or second partial carrier in the connection region. Preferably, the first partial carrier has an outlet at a distance from the region covered by the second partial carrier, optionally with a connection conduit connected thereto.

Recesses in carriers made of glass are preferably produced by irradiating the glass with laser radiation and subsequent etching.

Generally, in each embodiment, a first recess can be subdivided by a membrane which is preferably arranged in perpendicular to the first surface of the carrier so that it is e.g. arranged vertically when the carrier or its first surface is arranged horizontally. A membrane subdividing a first recess can be spanned, for example, by a frame which rests, for example, against surfaces of the carrier which lie between the cross-sectional openings of the second recesses.

In the method, generally liquid is introduced into the first recess, while liquid with at least one cell is contained in the second recesses. This is achieved, for example, by introducing liquid with cells selectively into second recesses, e.g. by means of a droplet generator or a metering device, which is in particular a nozzle. Alternatively, a liquid containing cells can be introduced into the first recess so that it distributes into the second recesses. For example, cells can distribute from the liquid into the second recesses. Optionally, the cell-containing liquid that remains in the first recess can subsequently be removed. Therein, the liquid, which is preferably a cell culture medium, can be present in admixture with cells suspended therein and can be introduced into the recesses as a mixture or suspension, or the liquid containing the cells can be introduced into recesses in a separate step and by means of a separate drop generator or a separate metering device, and a cell culture medium not containing cells can be introduced into recesses in a separate step, preferably subsequently, preferably by means of a separate metering device.

Presently, a cell culture medium comprises a medium that maintains cells viable, in particular plant cells, yeasts, bacteria or animal cells, preferably human cells, e.g. viable for at least 1 h, preferably for at least 12 h or at least 24 h or at least two days or at least three days or at least four days or at least five days or at least six days or at least seven days.

In an embodiment of the method in which the carrier optionally comprises or consists of only recesses in the form of the second recesses and further optionally at least one outlet, optionally at least one connection conduit connected thereto, liquid can be applied directly onto the cross-sectional openings of the second recesses lying in the plane of the first surface of the carrier. In an embodiment in which the carrier has only second recesses and medium protrudes beyond the plane of the cross-sectional openings of the second recesses, this protruding layer of medium forms the volume of the first recess and extends over the first thickness section so that this medium covers the second recesses. Therein, the medium can extend over a first thickness section of e.g. 1 $\mu$m to 3 mm, e.g. 10 $\mu$m to 200 $\mu$m above the second recesses. The liquid protruding beyond the plane of the first surface of the carrier can run off over the edge of the carrier, preferably along the at least one outlet and optionally along the connection conduit. Therein, this liquid can be induced to move by means of tilting the carrier, by applying a gas flow and/or vibration, e.g. ultrasound. In particular, in this embodiment, the first surface can be poorly wettable for aqueous liquids, e.g., be hydrophobic, e.g., be made of plastic or a textured, functionalized or coated glass surface. Liquid droplets applied to the first surface or to the plane in which the cross-sectional openings of the second recesses are located can undergo mass transfer with liquid present there when moving across this plane. For example, a droplet of medium applied to said plane as a rolling droplet can absorb and/or partially replace liquid already present, e.g., spent medium. Optionally, the surface of the carrier that is in the plane in which the cross-sectional openings of the second recesses are located can have channels introduced in the carrier, the cross-section of which channels is open to the plane, to direct the liquid extending over the plane as it moves. Therein, the liquid can be applied to said plane of the carrier in an intermittent or batch-wise manner as at least two droplets. When exceeding the volume of liquid above the plane in which the carrier extends, liquid will run off, in particular selectively through an outlet.

In general, liquid, preferably medium, extending over the first thickness section prevents evaporation of medium from the second recesses. Therein, the first thickness section can be a few micrometers to a few centimeters in size. Therein, the large volume of the first thickness section provides space for sufficient liquid in order to reduce the effects of nutrient consumption and accumulation of metabolites in the second recesses by diffusion. The large aspect ratio of the second recesses has the effect that movements of the liquid in the adjacent first thickness section or first recess will only marginally move the cells in the second recesses and the cells will not be flushed out of the second recesses.

For example, a first recess can be connected to 100000 second recesses, each second recess having a diameter of 54 $\mu$m, a depth of 436 $\mu$m, an aspect ratio of depth to diameter of 8:1, and a volume of 1 nl. The recesses are spaced apart from one another by, for example, 10 $\mu$m. In order to encompass all second recesses, the first recess must have an area of at least 410 mm². Conventionally, wells have much smaller aspect ratios, for example 0.16:1. At the same volume of 1 nl per well and a diameter of 200 $\mu$m, the depth is about 32 $\mu$m. In this case, 100,000 recesses occupy an area of 4410 mm², ten times the area of the large aspect ratio wells.

Due to the smaller surface area with the same volume per well, it is possible to monitor the contents of several wells in parallel with an optical microscope.

The large aspect ratio of the second recesses results in several advantages. For example, cell products, such as proteins or antibodies, can accumulate in the second recesses without or with slow removal of cell products. This can be used to analyze these cell products and the rate of production, e.g., by binding fluorescent markers and evaluating the intensity of the fluorescence. If cell products, e.g. metabolites, are removed faster than they are produced by the cells, ideal cultivation conditions can be generated. The alternation between slow and fast removal of cell products can be achieved, for example, by varying the inflow and outflow rates of the culture medium or other liquids.

The first recess can be formed in a plastic, metal, silicon, or glass part, e.g. in the form of a microtiter plate, in the form of a Petri dish, as a sealing ring or as a frame, also by combining different materials. The carrier can be connected to existing inlets and outlets in a cultivation station, especially for long-term cultivation. In addition, the temperature, the gas atmosphere, for example the $CO_2$ content, the composition of the liquids, the content of biomolecules or other substances can be adjusted at inlets or measured at outlets. Sensors that measure pH, fluorescence, concentrations, temperature, metabolites, biomolecules produced by cells, etc., can be attached to outlets.

Through one or more supply conduits, e.g. in the form of capillaries, various liquids can be added into the first recess, e.g. nutrient medium, buffer solutions, reagents, staining agents. These can contain cells. The liquids can be withdrawn again through one or more outlets to ensure continuous or intermittent or demand-controlled exchange. Supply conduits can be arranged so that the cells are not affected when liquids are supplied. When using a capillary as a supply conduit, liquid can be supplied in particular above a second recess that does not contain any cells.

Samples can be taken from the liquid in the first recess, for example for detecting products of the cells (proteins, antibodies, metabolites) at time intervals or continuously, to monitor the concentration of added reagents or to analyze exosomes or extracellular vesicles (EV), produced by cells, in particular the loading with type and amount of proteins and nucleic acids, to determine characteristics such as heterogeneity of the EV in their biological and physical properties (size, composition in type and amount, density, refractive index).

If multiple inlets are used, a part of them can be used for adding liquids containing no cells such as medium, water, etc. and another part can be used for adding cell-containing liquids.

When introducing liquid into the first recess or the second recesses, for example, a liquid of lower density than the cell-containing liquid, which is preferably immiscible with the cell-containing liquid, can serve as temporary evaporation protection. If the first thickness section is small enough, cells can be introduced through the liquid in the first thickness section into the second recesses. In parallel with the introduction of the cell-containing liquid, a second supply conduit can be used to compensate for evaporation. Optionally, the delivered liquid can be continuously changed in its composition to exchange the medium surrounding the cells over a period of time.

The carriers in various embodiments are adapted such that cells can be cultured in the second recesses. Additionally, methods for analyzing the cells can be carried out. In particular, cells can be stained by a staining agent. By ensuring an exchange of the liquids in the vicinity of the cells, the staining agent can subsequently be washed out without removing or otherwise affecting the cells.

Various methods for cell cultivation can be applied. In particular, cells can be printed into the second recesses with very little liquid and subsequently adding medium. Alternatively, medium can be supplied first and subsequently by cell-containing liquid. Alternatively, cell-containing medium can be supplied in one step. In order to ensure that the cells settle in the second recesses, waiting can be done between method steps. Additionally, the settling of the cells can be assisted by centrifuging or agitating, in particular shaking or vibrating the carrier. Thereby, additionally gas bubbles in the second recesses can be removed. Subsequently, cell-containing medium can be removed until cells are essentially present only within the second recesses.

FIG. 1 shows a carrier 1 in cross-section, consisting of a first partial carrier 2 and an adjoining second partial carrier 3, wherein in the first partial carrier 2 a first recess 4 is formed which covers the cross-sectional openings 5 of the adjoining second recesses 6. Therefore, the inner volumes of the second recesses 6 are in contact with the inner volume of the first recess 4 along their cross-sectional openings 5, which contact allows for a mass transfer between them, in particular by diffusion. The second recesses 6 extend over a second thickness section 8 of the carrier 1, in this case over a second thickness section 8 in the second partial carrier 2. In the first partial carrier 2, the first recess 4 extends over the first thickness section 7, which therein is equal to the thickness of the first partial carrier 2. In its first thickness section 7, here equal to the first partial carrier 2, the carrier 1 has an outlet 9 through which liquid F whose level reaches the cross-section of the outlet 7 can exit. A supply conduit 10 opens at a distance above the plane over which the outlet 9 extends. The supply conduit 10 is not necessarily connected to the carrier, but can be guided independently of the carrier, for example by means of a traversing device (not shown).

The large aspect ratio of the second recesses 6 allows movement of the liquid in the first recess 4 without flushing cells Z located at the bottom 14 or in the volume of the second recess 6 out of the second recesses, respectively, while minimizing any influence of turbulence on the cells.

Figure 2:
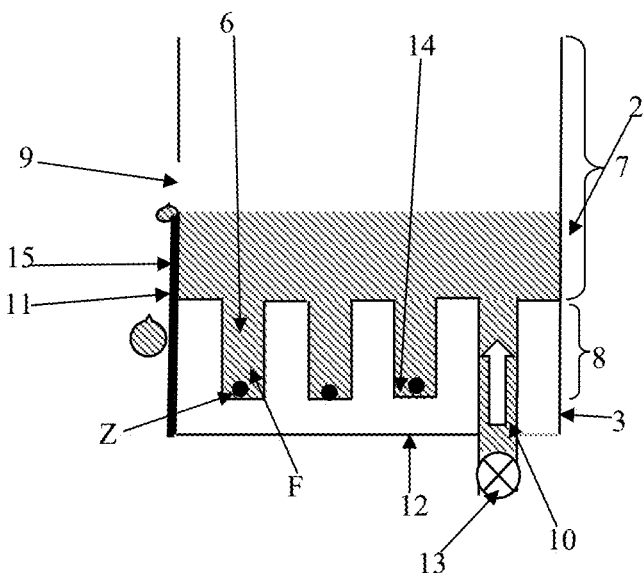

FIG. 2 shows a carrier 1 in cross-section which, like the carrier 1 shown in FIG. 1, consists of a first partial carrier 2 having a first recess 4 and a second partial carrier 3 attached thereto, in which second recesses 6 adjacent to the first recess 4 extend over the second thickness section 8. An outlet 9 is formed in the first partial carrier 2. The outlet 9 shown in FIGS. 1 and 2 extends along an outer end surface 11 of the carrier 1. A supply conduit 10 extends from the second surface 12 of the carrier 1 or its second partial carrier 3 into the first recess 4. As preferred, the supply conduit 10 comprises a controlled valve 13 to control the supply of liquid F into the first recess 4.

Figure 3:
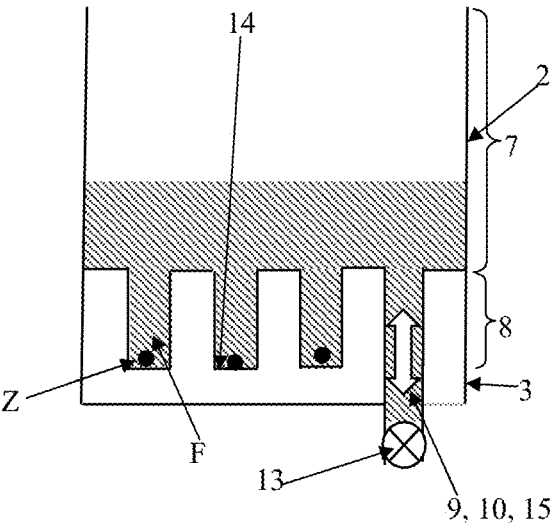

FIG. 3 shows an embodiment of the carrier 1 in which a connection conduit 15 forming an outlet 9 and, in opposite flow forming a supply conduit 10, extends through the carrier 1 from the first recess 4 to the second surface 12 thereof. Such a connection conduit 15 forming both a supply conduit 10 and an outlet 9, preferably has a controlled valve 13, which further preferably has two or more connected conduits, of which e.g. one is connected to a storage container for medium and another is connected to a collecting container for liquid F discharged from the first recess 4. This embodiment can also be provided with a lid covering the first recess. Preferably, the lid then has a valve by which the composition of the gas atmosphere can be controlled.

Figure 4:
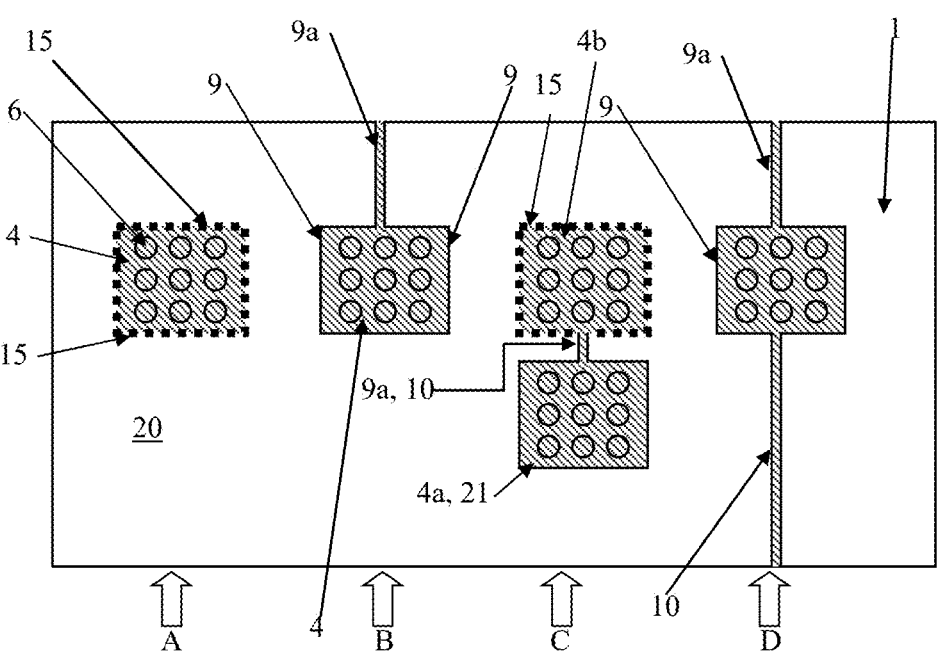

FIG. 4 shows embodiments of the invention in a one-piece carrier 1 in plan view onto the first surface 20 of the carrier 1 and onto the cross-sectional opening of a respective first recess 4. The first recess 4, here rectangular, extends over the cross-sectional openings of the adjacent second recesses 6, which are formed as an arrangement of 3×3 second recesses 6 per first recess 4.

In an embodiment A of FIG. 4, the first recess 4 is surrounded by connection conduits 15 passing through the carrier 1 and connected to an outlet 9 or forming the outlet 9. The connection conduits 15 extend from the first recess through the carrier 1 to its second surface 12 opposite the cross-sectional opening of the first recess 4. The connection conduits 15 passing through the carrier 1 selectively guide liquid emerging from the first recess to the opposite second surface 12 of the carrier 1, so that the liquid can be selectively removed there and also does not contaminate another first recess 4 formed in the same carrier 1.

In an embodiment B of FIG. 4, a first recess 4 is connected to an outlet 9 which is formed in the carrier 1 in the form of a trench whose cross-section extends into the carrier 1. At the circumference of the carrier 1 the outlet 9 is connected to a connection conduit 15, which extends along the circumferential end wall of the carrier 1 onto its second surface 12.

In an embodiment C of FIG. 4, a first recess 4a is enclosed by a circumferential outlet 9 which by a conduit section 9a forms an inlet into a further first recess 4b so that liquid F can flow through the outlet 9 and its conduit section 9a from a first recess 4a into a further first recess 4b. The first recess 4b is enclosed by connection conduits 15 through which liquid F emerging from this first recess 4b is directed to the opposite second surface 12 of the carrier 1. This embodiment also shows, as an example of a storage recess 21, a first recess 4a connected by a supply conduit 10 to another first recess 4b.

In an embodiment C of FIG. 4, cells producing certain biomolecules, e.g. cytokines, antibodies, proteins, can be cultivated in the second recesses 6 allocated to a first recess 4. Through the conduit section 9a, these molecules can be transported to another first recess 4 and be detected there or act on other cells.

In an embodiment D of FIG. 4, as also described with reference to embodiment B, a first recess 4 is connected to an outlet 9 formed in the carrier 1 in the form of a trench whose cross-section extends into the carrier 1. At the circumference of the carrier 1 the outlet 9 is connected to a connection conduit 15 which along the circumferential end wall 11 of the carrier 1 extends onto the second surface 12 thereof. On the wall of the first recess 4 opposite the outlet 9, a supply conduit 10 is formed in the carrier 1, also in the form of a trench. The carrier 1 can have one or more first recesses 4 of the same or different shape, e.g. of the FIGS. 4A to 4D. In the case of multiple first recesses 4, different liquids or the same liquids in different concentrations or combination thereof can be contained in different first recesses 4. Different cell types can be contained in second recesses 6 belonging to different first recesses 4.

FIG. 5 shows an embodiment in which the wall extending over the first thickness section 7 and having or enclosing a first recess 4 can be formed by a first partial carrier 2 adjacent to a second partial carrier 3 in which an arrangement of second recesses 4 is formed. A supply conduit 10, which is preferably connected to a connection conduit 15, can open into the first partial carrier 2 and, preferably opposite to the supply conduit 10, an outlet 9 can be formed, which is preferably connected to a connection conduit 15. The supply conduit 10 shown here and the connection conduit 15 are each provided with a controlled valve 13, which allows control of the supply and discharge of liquid F into or resp. out of the first recess 4.

As shown in FIG. 6, the first partial carrier 2 can be displaceable relative to the second partial carrier 3, e.g. in that the first partial carrier 2 and the second partial carrier 3 overlap in their edge regions in a displaceable and liquid-tight manner. A seal 16 can be arranged between the first partial carrier 2 and the second partial carrier 3, which seal 16 e.g. is a ridge of plastic or a rubber ring on the first partial carrier 2 or second partial carrier 3. Further, FIG. 6 shows that the first partial carrier 2 can cover the first recess 4. The covering portion of the first partial carrier 2 can be carried out as a cover which can be recycled.

FIG. 7 shows a method for separately introducing cell-containing liquid by means of a first metering device 17 and, prior thereto, subsequently or simultaneously, introducing cell-free medium by means of a second metering device 18, into recesses 4, 6 of the carrier 1.

FIG. 7 shows a carrier 1 whose recesses consist of an arrangement of second recesses 6 and a layer of liquid covering them, which forms the first thickness section 7 that is held in place by surface tension. For this purpose, it is preferred that the enclosure of the arrangement of second recesses 6 is hydrophobic, for example has a hydrophobic coating. The carrier 1 has as outlet 9, for example, a hydrophilic region adjacent to a connection conduit 15 which extends along the end surface 11 of the carrier 1 to its second surface 12 opposite to the cross-sectional openings of the recesses 6. Preferably, the hydrophobic coating enclosing the second recesses 6 is set up such that droplets of a liquid placed on the carrier converge to form a coherent layer and only then run off at the outlet 9. Alternatively, the outlet 9 can be formed by microstructures in the surface of the carrier 1.

In the method, the running off of the liquid over the outlet 9 can be controlled by tilting the carrier 1 or by bringing the liquid into contact with a device having capillary action.

FIG. 8 shows a carrier 1 in whose first partial carrier 2 optionally there is arranged no outlet 9, but the inlet 10 simultaneously serves as a metering device 17 and as an outlet 9. Alternatively, inlet and outlet can be realized as two metering devices 17, 18. The first recess is subdivided in perpendicular to the cross-sectional opening of the first recess by a membrane 19, which is preferably semi-permeable, whereby the common liquid volume of the first recess 4 is subdivided above the second recesses 6. The membrane 19 can also be combined in an analogous manner with other embodiments and there subdivide the first recess 4 or the first thickness section 7.

FIG. 9A shows a two-pieced embodiment of a carrier 1 of a first partial carrier 2 and a second partial carrier 3 attached thereto in a liquid-tight manner. In the case of first and second partial carriers 2, 3 made of glass or silicon, these can be joined together, for example, by bonding. In this embodiment, the second recesses 6 are spaced from a first recess 4 and connected thereto by means of the transition conduit 23. The first recess 4 can have any diameter independent of the second recesses 6. Therein, the transition conduit 23 is formed by a bottom recess 24, which forms a region-wise spacing between the first partial carrier 2 and the second partial carrier 3. The first recess 4 and the second recesses 6 are formed as through holes in the first partial carrier 2, the bottoms of the first and second recesses 4, 6 are each formed by the second partial carrier 3. Therein, the first thickness section 7 is preferably equal to the second thickness section 8. The second partial carrier 3 has a bottom recess 24 which at the height of the cross-section of the transition conduit 23 extends into the second partial carrier. The first partial carrier 2 is connected to the second partial carrier 3 along the sections of the second partial carrier 3 protruding beyond the bottom recess 24. The bottom recesses 24 form a connection conduit having a diameter smaller than the diameter of the cells in order to retain them in the second recesses 6. Through the bottom recesses 24, the exchange of the liquids takes place, whereby the interference with the cells is minimized.

This embodiment has the advantage that the cross-sectional openings 5 of the second recesses 6 are directly open and accessible, and the second recesses 6 are also in liquid communication with the first recess 4 through the transition conduit 23.

FIG. 9B shows a carrier 1, in plan view onto the cross-sectional openings 5 of second recesses 6 and onto the cross-sectional opening of a first recess 4. The transition conduits 23 shown here in hatched lines are concealed by the first partial carrier 2. The cross-section along A-A through the first partial carrier 2 is shown in FIG. 9A in the first partial carrier 2.

FIG. 9C shows a top view of a first partial carrier 2 in which both the first recess 4 and the second recesses 6 are formed as spaced-apart through holes.

The second partial carrier 3 has one or more bottom recesses 24 which extend into a constant depth and which are covered by the cross-sections of at least one first recess 4 and at least two second recesses 6 and which forms a transition conduit 23 connecting a first recess 4 to the second recesses 6.

Figure 10:
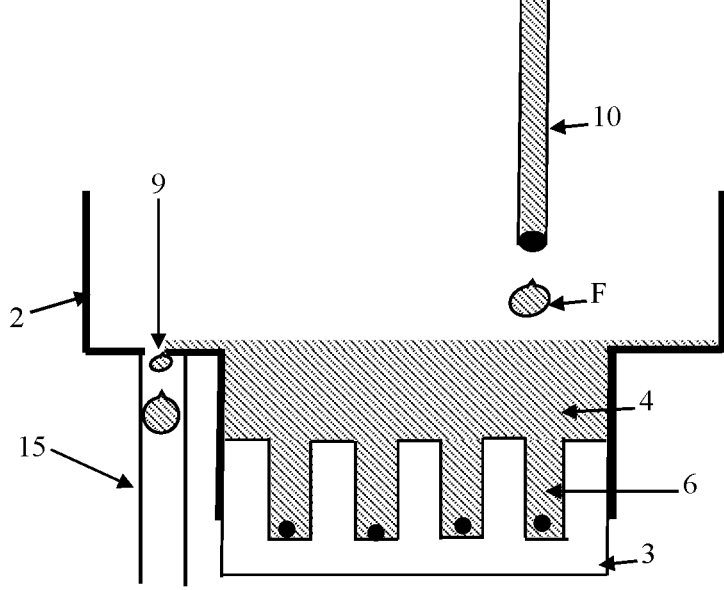

FIG. 10 shows an embodiment in which the carrier 1 consists of a first partial carrier 2, preferably made of plastic, and a second partial carrier 3, preferably made of glass, the first partial carrier 2 being connected to the second partial carrier 3 along the circumference thereof. A first recess 4 extends over second recesses 6 formed in the second partial carrier 3. The first partial carrier 2 has an outlet 9 at a distance from the region of its first recess 4, preferably at a distance from the region covered by the second partial carrier 3. A supply conduit 10 opens at a distance above the first recess 4 to meter drops of liquid F into the first recess 4. Preferably, the first partial carrier 2 opposite to the second partial carrier 3 has a cross-sectional opening, into which or against which the supply conduit 10 is directed. Preferably, a connection conduit 15 is connected to the outlet 9.

Figure 11A:
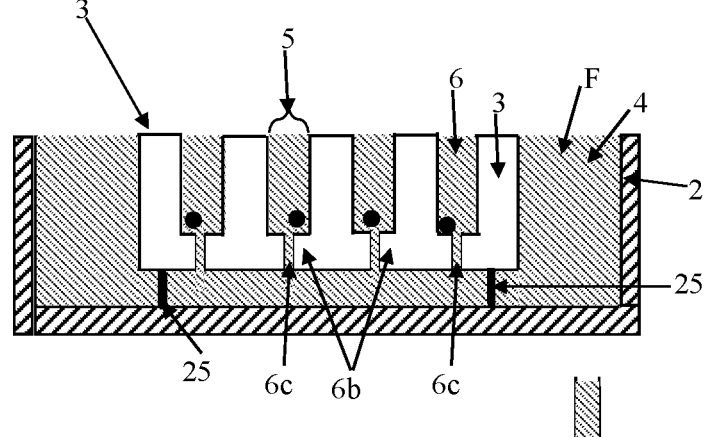
Figure 11B:
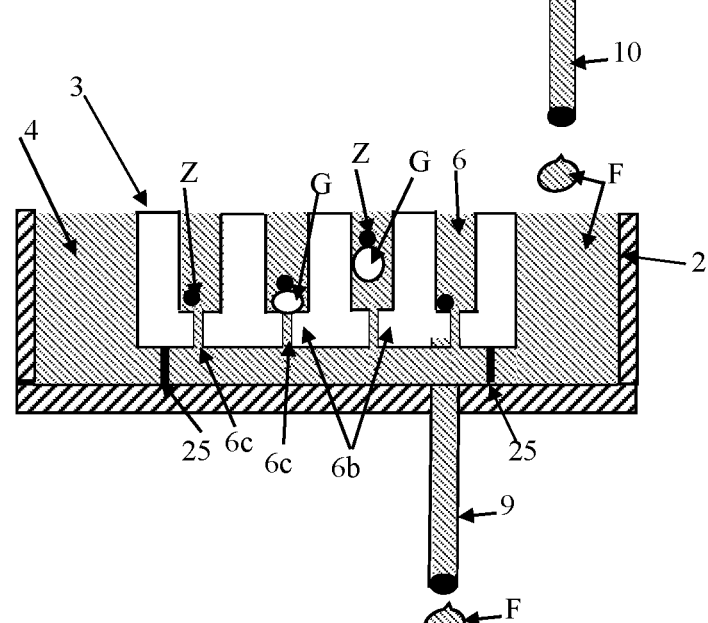

FIGS. 11A and 11B show embodiments in which a second partial carrier 3 is arranged at least partially or completely within the first recess 4 of a first partial carrier 2, wherein the cross-sectional openings of the first recess 4 and the cross-sectional openings of the second recesses 6 are arranged in parallel to one another and preferably lie in a common plane. When the first and second partial carriers 2, 3 are arranged horizontally, the cross-sectional openings of the first recess 4 and the cross-sectional openings of the second recesses 6 are horizontal and open at the top. The second recesses 6 each have at least one through hole 6c in their bottoms 6b, so that each second recess 6 communicates with the first recess 4 through at least one through hole 6c even if the second partial carrier 3 protrudes over the cross-sectional opening of the first recess 4 and/or over the level of the liquid F in the first recess 4. The bottoms 6b of the second recesses 6 formed in the second partial carrier 3 are spaced from the first partial carrier 2, preferably spacers 25 are arranged between the bottoms 6b of the second partial carrier 6 and the first partial carrier 2. The through holes 6c preferably each have cross-sections smaller than cells Z. The through holes 6c can be coated, e.g. hydrophobically, to prevent or assist the exchange of certain liquids.

As shown in FIG. 11B, the first partial carrier 2 can have an outlet 9 arranged, for example, below the second partial carrier 3. A connection conduit 15 can be connected to the outlet 9. Optionally, the connection conduit 15 can also form a supply conduit 10. Alternatively or additionally, a supply conduit 10 can open above the first partial carrier 2 in order to meter liquid F into the first recess 4.

The embodiments in FIGS. 11A and B are particularly suitable for separating cells and cell products from one another.

In the method, the second recesses 6 and the first recess 4 are filled with liquid F, which is in particular medium, and are in contact with one another through the through holes 6c. In particular in an embodiment in which a supply conduit 10 opens below the second recesses 6 or below the second partial carrier 3 in the first partial carrier 2, a gas, e.g. inert gas or air, e.g. air or oxygen for cell cultivation, optionally air or $O_2$ with 5% $CO_2$, can be introduced through the supply conduit 10 in addition to or as an alternative to liquid F. The gas can be introduced in a bubble-free manner by the volumetric flow of the gas being sufficiently small. Alternatively, the gas can be supplied with a volumetric flow sufficient to form bubbles, wherein liquid F is moved in the second recesses and optionally cells Z are floated by means of the gas bubbles G. Gas bubbles can alternatively be generated by cavitation induced by laser radiation.

By pressure changes, cells Z can be moved away from the through holes 6c to aid in the exchange of the liquids.

Figure 12:
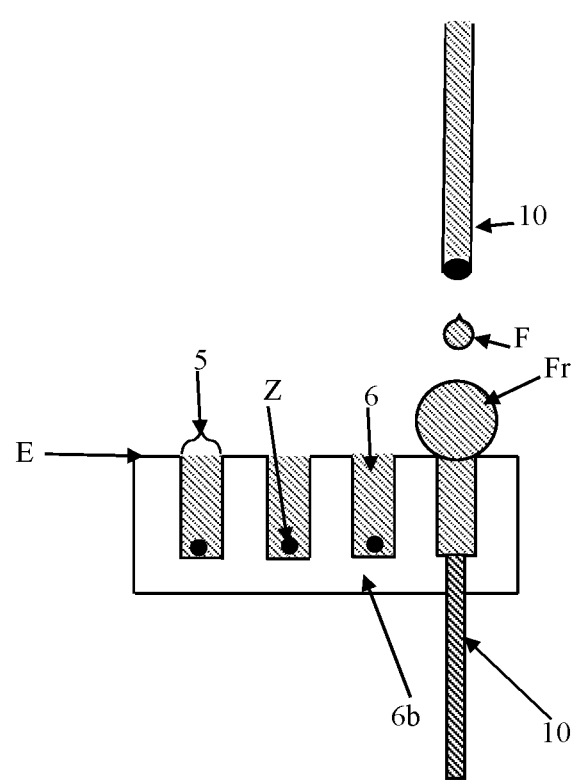

FIG. 12 schematically shows an embodiment in which the carrier 1 consists of a second partial carrier 3 having second recesses 6, the cross-sectional openings 5 of which and regions of the surface of the carrier 1, 3 between these cross-sectional openings 5 lie in a common plane E. In particular, if these surface regions between the cross-sectional openings 5 have a surface energy that does not permit wetting by the liquid F or permits it only to a small extent, for example surface regions made of plastic or functionalized, coated or hydrophobically structured glass, a liquid F moving across the plane E, for example in the form of a rolling drop Fr, can take up spent medium from the second recesses 6 and at least partially replace it. A rolling drop Fr can be introduced, for example, by applying liquid F in the form of a plurality of drops onto the plane E or into second recesses 6, e.g. through a supply conduit 10 opening into a second recess 6, as e.g. shown in FIG. 2. Liquid F projecting above the plane E, in particular in the form of a rolling drop Fr, can be driven by tilting the carrier 1 against the horizontal, by accelerating and/or vibrating the carrier, by applying a gas flow.

Generally, in embodiments in which the carrier consists of a second partial carrier 3 having second recesses 6 therein, the second partial carrier can be referred to as the carrier 3 having recesses 6 therein.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

| Reference sign: | |
|---|---|
| 1 carrier | 10 supply conduit |
| 2 first partial carrier | 11 end wall, end surface |
| 3 second partial carrier | 12 second surface of the carrier |
| 4, 4a, 4b first recess | 13 controlled valve |
| 5 cross-sectional opening of a second recess | 14 bottom of the second recess |
| 6 second recess | 15 connection conduit |
| 6b bottom of a second recess | 16 seal |
| 6c through hole | 17 first metering device |
| | 18 second metering device |

16

-continued

| Reference sign: | |
|---|---|
| 7 first thickness section | 19 membrane |
| 8 second thickness section | 20 first surface of the carrier |
| 9 outlet | 21 supply recess |
| 9a conduit section of the outlet | 22 material |
| 23 transition conduit | F liquid |
| 24 bottom recess in second partial carrier | Fr rolling drop |
| 25 spacer | Z cell |
| E plane | G gas bubble |

The invention claimed is:

1. A carrier for cultivating cells, comprising at least one first recess extending over a first thickness section from a first surface up to a second thickness section adjacent to the first thickness section, an arrangement of second recesses in the second thickness section and extending from the first recess, wherein the second recesses comprise a bottom, wherein the second recesses comprise an aspect ratio of depth to diameter of at least 1:1 and a diameter of at most 1 mm, the carrier comprising an outlet whose cross-section opens in or adjacent to the first thickness section, the carrier comprising a connection conduit connected to the outlet and extending to a second surface that lies opposite the first surface.

2. The carrier according to claim 1, wherein the outlet comprises a cross-section projecting into the carrier and open to the plane of the first surface.

3. The carrier according to claim 1, wherein the connection conduit extends along an end wall of the carrier o through the carrier.

4. The carrier according to claim 1, comprising a supply conduit in the first surface or in the first thickness section, the supply conduit opening into the first recess.

5. A carrier for cultivating cells, comprising at least one first recess extending over a first thickness section from a first surface up to a second thickness section adjacent to the first thickness section, an arrangement of second recesses in the second thickness section and extending from the first recess, wherein the second recesses comprise an aspect ratio of depth to diameter of at least 1:1 and a diameter of at most 1 mm, the carrier comprising an outlet whose cross-section opens in or adjacent to the first thickness section, the carrier comprising a connection conduit connected to the outlet and extending to a second surface that lies opposite the first surface, wherein the outlet and the connection conduit are adjacent each other and comprise a hydrophilic surface, and wherein regions of the first surface and/or regions of the second surface are hydrophobic.

6. A carrier for cultivating cells, comprising at least one first recess extending over a first thickness section from a first surface up to a second thickness section adjacent to the first thickness section, an arrangement of second recesses in the second thickness section and extending from the first recess, wherein the second recesses comprise an aspect ratio of depth to diameter of at least 1:1 and a diameter of at most 1 mm, the carrier comprising an outlet whose cross-section opens in or adjacent to the first thickness section, wherein the carrier is defined in a single piece of glass.

7. A carrier for cultivating cells, comprising at least one first recess extending over a first thickness section from a first surface up to a second thickness section adjacent to the first thickness section, an arrangement of second recesses in the second thickness section and extending from the first recess, wherein the second recesses comprise an aspect ratio of depth to diameter of at least 1:1 and a diameter of at most 1 mm, the carrier comprising an outlet whose cross-section opens in or adjacent to the first thickness section, consisting of a second partial carrier extending over the second thickness section and of a first partial carrier extending over the first thickness section, the first and second partial carriers being arranged in a liquid-tight manner relative to one another.

8. The carrier according to claim 7, wherein the first and the second partial carriers are arranged displaceably against one another.

9. The carrier according to claim 7, wherein one or both of the first and second partial carriers consists of glass, plastic and/or silicon.

10. The carrier according to claim 7, wherein the second partial carrier is arranged at least partially within the first recess of the first partial carrier, the second recesses each having at least one through hole boring in their bottoms, so that each second recess is connected to the first recess through at least one through hole boring.

11. The carrier according to claim 7, wherein the first recesses and second recesses are formed as spaced-apart through holes in the first partial carrier and are connected to one another by transition conduits formed by a bottom recess, which is formed as a region-wise spacing between the first partial carrier and the second partial carrier.

12. The carrier according to claim 11, wherein the first thickness section is equal to the second thickness section and the second partial carrier has a bottom recess extending into the second partial carrier by the height of the cross-section of the transition conduit, the first partial carrier being connected to the second partial carrier along regions of the second partial carrier projecting beyond the bottom recess.

13. A method for cultivating cells, comprising introducing liquid in which cells are suspended into second recesses of the carrier according to claim 7, and subsequent remaining of liquid from the first thickness section along the outlet and the connection conduit.

14. The method according to claim 13, wherein the first partial carrier is formed only by the surface of the second partial carrier by which the second recesses are spaced apart, and the first recess adjacent to the arrangement of second recesses is formed solely by a liquid layer generated by surface tension.

15. The method according to claim 13, wherein the carrier has only second recesses and medium forms a layer projecting above the plane of the cross-sectional openings of the second recesses, which layer forms the volume of the first recess.

16. The method according to claim 13, wherein the carrier comprises recesses whose cross-sectional openings are spaced apart by surface regions of the carrier, these surface regions and the cross-sectional openings of the recesses lying in a common plane, wherein liquid is applied onto this plane and the liquid is moved along the carrier by tilting the carrier against the horizontal, by vibrating the carrier, and/or by applying pressurized gas to the plane.

17. A carrier for cultivating cells, comprising at least one first recess extending over a first thickness section from a first surface up to a second thickness section adjacent to the first thickness section, an arrangement of second recesses in the second thickness section and extending from the first recess, wherein the second recesses comprise an aspect ratio of depth to diameter of at least 1:1 and a diameter of at most 1 mm, the carrier comprising an outlet whose cross-section opens in or adjacent to the first thickness section, comprising at least two first recesses, each of which is enclosed by circumferentially arranged connection conduits extending through the carrier.

18. A carrier for cultivating cells, comprising at least one first recess extending over a first thickness section from a first surface up to a second thickness section adjacent to the first thickness section, an arrangement of second recesses in the second thickness section and extending from the first recess, wherein the second recesses comprise an aspect ratio of depth to diameter of at least 1:1 and a diameter of at most 1 mm, the carrier comprising an outlet whose cross-section opens in or adjacent to the first thickness section, comprising at least two first recesses, at least one of which is enclosed by an outlet in the form of a trench that opens into another one of the at least two first recesses, which is enclosed by circumferentially arranged connection conduits extending through the carrier.

19. A carrier for cultivating cells, comprising at least one first recess extending over a first thickness section from a first surface up to a second thickness section adjacent to the first thickness section, an arrangement of second recesses in the second thickness section and extending from the first recess, wherein the second recesses comprise an aspect ratio of depth to diameter of at least 1:1 and a diameter of at most 1 mm, the carrier comprising an outlet whose cross-section opens in or adjacent to the first thickness section, comprising a controlled valve is arranged in an outlet, in a connection conduit, and/or in a supply conduit.

* * * * *